United States Patent
Allen et al.

(10) Patent No.: US 10,353,107 B2
(45) Date of Patent: Jul. 16, 2019

(54) PETROPHYSICALLY REGULARIZED TIME DOMAIN NMR INVERSION

(71) Applicants: SCHLUMBERGER TECHNOLOGY CORPORATION, Sugar Land, TX (US); SAUDI ARABIAN OIL COMPANY, Dhahran (SA)

(72) Inventors: David F. Allen, Katy, TX (US); George Bordakov, Richmond, TX (US); Steve F. Crary, Sugar Land, TX (US); Philip Savundararaj, Richmond, TX (US); Ramsin Eyvazzadeh, Al-Khobar (SA); Edward Alan Clerke, Dhahran (SA); Johannes J. Buiting, Didam (NL); Paul Smith, Al-Khobar (SA); Jim Funk, Al-Khobar (SA)

(73) Assignees: SCHLUMBERGER TECHNOLOGY CORPORATION, Sugar Land, TX (US); SAUDI ARABIAN OIL COMPANY, Dhahran (SA)

( * ) Notice: Subject to any disclaimer, the term of this patent is extended or adjusted under 35 U.S.C. 154(b) by 665 days.

(21) Appl. No.: 14/355,498

(22) PCT Filed: Oct. 31, 2012

(86) PCT No.: PCT/US2012/062699
§ 371 (c)(1),
(2) Date: Apr. 30, 2014

(87) PCT Pub. No.: WO2013/066949
PCT Pub. Date: May 10, 2013

(65) Prior Publication Data
US 2014/0285190 A1 Sep. 25, 2014

Related U.S. Application Data

(60) Provisional application No. 61/553,650, filed on Oct. 31, 2011.

(51) Int. Cl.
*G01V 3/32* (2006.01)
*G01N 24/08* (2006.01)
(Continued)

(52) U.S. Cl.
CPC ............ *G01V 3/32* (2013.01); *G01N 24/081* (2013.01); *G01R 33/44* (2013.01); *G01R 33/4625* (2013.01)

(58) Field of Classification Search
CPC ........ G01V 3/32; G01N 24/081; G01R 33/44; G01R 33/4625
(Continued)

(56) References Cited

U.S. PATENT DOCUMENTS 6,094,048 A * 7/2000 Vinegar ............... G01N 24/081
324/303
6,115,671 A * 9/2000 Fordham ............. G01N 24/081
324/303

(Continued)

OTHER PUBLICATIONS

Ahr, et al., "Confronting the carbonate conundrum", Oilfield Review, Spring 2005, vol. 17, No. I, pp. 18-29.
(Continued)

*Primary Examiner* — Susan S Lee
(74) *Attorney, Agent, or Firm* — Michael Dae (57) ABSTRACT

A petrophysically regularized time domain nuclear magnetic resonance (NMR) inversion includes using an NMR tool to acquire NMR data and inverting the acquired NMR data in a time domain using petrophysical constraints. The inverted NMR data is analyzed. The petrophysical constraints may be identified by: determining a number of porobodons to seek, defining a plurality of zones in which only a subset of porobodon sets is present, and stacking all NMR echoes in each zone satisfying discriminators. The number of porobodons to seek may be based on knowledge of core samples, logs, and NMR sensitivity. The discriminator logs may be logs sensitive to porosity partitioning. A computing system having a processor, a memory, and a program stored in memory may be configured to perform the method. The system may be conveyed downhole on a wireline, a while-drilling drill string, a coiled tubing, a slickline, or a wired drill pipe.

13 Claims, 7 Drawing Sheets

(51) Int. Cl.
*G01R 33/44* (2006.01)
*G01R 33/46* (2006.01)

(58) Field of Classification Search
USPC ............................................. 324/303
See application file for complete search history.

(56) References Cited

U.S. PATENT DOCUMENTS

| | | | |
|---|---|---|---|
| 6,232,778 B1 | 5/2001 | Speier et al. | |
| 6,600,316 B2* | 7/2003 | Chen ..................... | G01V 3/32 324/303 |
| 7,133,777 B2 | 11/2006 | Goswami et al. | |
| 7,538,547 B2 | 5/2009 | Heaton | |
| 2002/0175682 A1* | 11/2002 | Chen ..................... | G01V 3/32 324/303 |
| 2003/0107374 A1* | 6/2003 | Chen ..................... | G01N 24/081 324/303 |
| 2005/0040822 A1* | 2/2005 | Heaton .................. | G01V 3/32 324/307 |
| 2006/0122779 A1* | 6/2006 | Minh ..................... | G01V 3/32 702/11 |
| 2008/0154509 A1* | 6/2008 | Heaton .................. | G01V 11/00 324/303 |
| 2009/0125239 A1* | 5/2009 | Niemeyer ............. | G01N 24/081 324/303 |
| 2009/0157350 A1 | 6/2009 | Salazar-Tio et al. | |
| 2010/0010744 A1* | 1/2010 | Prange .................. | G01V 3/32 324/303 |
| 2011/0025324 A1 | 2/2011 | Fransson et al. | |
| 2011/0215802 A1* | 9/2011 | Venkataramanan ..... | G01V 3/32 324/303 |

OTHER PUBLICATIONS

Allen, et al., "The Practical Application of NMR Logging in Carbonates: 3 Case Studies", SPWLA 42nd Annual Logging Symposium, Jun. 17-20, 2001, 14 pages.
Clerke, et al., "Beyond Porosity-Permeability Relationships-Determining Pore Network Parameters for the Ghawar Arab-D Using the Thomeer Method", 6th Middle East Geosciences Conference, 2004, GeoArabia, vol. 9, Issue: 1, 6 pages.
Clerke, et al., "Application of Thomeer Hyperbolas to decode the pore systems, facies and reservoir properties of the Upper Jurassic Arab D limestone, Ghawar field, Saudi Arabia: A "Rosetta Stone" approach", GeoArabia, 2008, vol. 13, Issue: 4, pp. 113-160.
Clerke, et al., "Permeability and Microscopic Displacement Efficiency of M_1 Bimodal Pore Systems in Arab D Limestone", 15th SPE Middle East & Oil Gas Show and Conference, SPE 105259-MS, Mar. 11-14, 2007, 12 pages.
Clerke, et al., "Permeability, Relative Permeability, Microscopic Displacement Efficiency and Pore Geometry of M_1 Bimodal Pore Systems in Arab-D Limestone", SPE Journal 105259-PA, Sep. 2009, p. 524-531.
Clerke, et al., "Beyond Porosity-Permeability Relationships: Determining Pore Network Parameters for the Ghawar Arab-D Using the Thomeer Method", GeoFrontier, Sep. 2003, vol. 1, Issue: 3, pp. 12-17.
Freedman, et al., "Processing of Data From an NMR Logging Tool", SPE Annual Technical Conference and Exhibition, SPE 30560, Oct. 22-25, 1995, pp. 301-316.
Genty, et al., "Distinguishing Carbonate Reservoir Pore Facies with Nuclear Magnetic Resonance Measurements", Natural Resources Research, Mar. 2007, vol. 16, No. 1, pp. 45-54.
Heaton, et al., "Saturation and viscosity from multidimensional nuclear magnetic resonance logging", SPE Annual Technical Conference and Exhibition, SPE 90564, Sep. 26-29, 2004, 11 pages.
Minh, et al., "Planning and Interpreting NMR Fluid-Characterization Logs", SPE Annual Technical Conference and Exhibition, SPE 84478, Oct. 5-8, 2003, 12 pages.
Newberry, et al., "Analysis of Carbonate Dual Porosity Systems from Borehole Electrical Images", Permian Basin Oil and Gas Recovery Conference, SPE 35158, Mar. 27-29, 1996, pp. 123-129.
Parker, et al., "Assigning uncertainties in the inversion of NMR relaxation data", Journal of Madnetic Resonance, Jun. 2005, vol. 174, Issue: 2, pp. 314-324.
Prange, et al., "Understanding NMR T2 spectral uncertainty", Journal of Magnetic Resonance, May 2010, vol. 204, Issue:1, pp. 118-123.
Price, et al., "Differential Evolution. A Practical Approach to Global Optimization", Springer-Verlag, Berlin, Heidelberg, 2005, pp. 287-295.
Akkurt, et al., "The Key to Improving the Vertical Resolution of Multi-Frequency NMR Logging Tools", SPWLA 42nd Logging Symposium, Jun. 17-20, 2001, 11 pages.
Salazar-Tio, et al., "Monte Carlo Optimization-Inversion Methods for NMR", Petrophysics, 2010, vol. 51, Issue: 3, pp. 208-218.
Venkataramanan, et al., "Mellin transform of CPMG data", Journal of Magnetic Resonance, Sep. 2010, vol. 206, Issue: 1, pp. 20-31.
International Search Report for International Application No. PCT/US2012/062699 dated Nov. 8, 2013.
Written Opinion for International Application No. PCT/US2012/062699. Nov. 8, 2013.

* cited by examiner

PETROPHYSICALLY REGULARIZED TIME DOMAIN NMR INVERSION

BACKGROUND

Nuclear magnetic resonance (NMR) can be used to determine various characteristics of porous subsurface formations and/or samples. NMR logging tools can be used downhole to obtain these fluid-filled pore system characteristics, which then can be used to assist in the determination of, for example, the presence, absence, location, mobility, and producibility of hydrocarbons in a given formation or sample.

Conventional NMR logging generally involves deploying in a wellbore an NMR instrument, which uses magnetic fields to generate and detect various radio frequency (RF) signals from nuclei in a formation or sample. Certain archetypal NMR techniques are described in U.S. Pat. No. 6,232,778, the entire disclosure of which is hereby incorporated by reference.

NMR measurements, in general, are accomplished by causing the magnetic moments of nuclei in a formation to precess about an axis. The axis about which the nuclei precess may be established by applying a strong, polarizing, static magnetic field $B_0$ to the formation, such as through the use of permanent magnets. This field causes the proton spins to align in a direction parallel to the applied field. This is sometimes referred to as the creation of longitudinal magnetization, resulting in the nuclei being "polarized". Polarization does not occur immediately, but instead grows in accordance with a spin-lattice relaxation time constant T1, and may take as long as several seconds to occur. After sufficient time, a thermal equilibrium polarization parallel to $B_0$ is established.

Next, a series of RF pulses are produced so that an oscillating magnetic field, $B_1$, is applied. The first RF pulse must be strong enough to rotate the magnetization from $B_0$ substantially into the transverse plane (i.e., transverse magnetization). Additional RF pulses are applied to create a series of spin echoes which bear information about various properties of the sample of interest such as volumes of liquids, their relaxation times, and diffusion properties. The frequency of the RF pulses is chosen to excite specific nuclear spins of a particular region of the sample that is being investigated. The time sequences and phases of the RF pulses are chosen to illuminate particular properties of the sample.

Two time constants are associated with the relaxation processes of longitudinal and transverse magnetization: T1 and T2. The spin-lattice relaxation time (T1) is the time constant for longitudinal magnetization to return to its thermal equilibrium value in the static magnetic field. The spin-spin relaxation time (T2) is the time constant for the transverse magnetization to return to its thermal equilibrium value of zero. In addition, diffusion coefficients of the liquids in the investigated sample affect the relaxation process as well. Distributions of these relaxation times are inferred from the amplitudes of the spin echoes mentioned above by T1, T2, and diffusion inversions, which can provide both one-dimensional distributions of any of those quantities and/or multi-dimensional joint distributions of any subset of them.

SUMMARY

A petrophysically regularized time domain nuclear magnetic resonance (NMR) inversion includes using an NMR tool to acquire NMR data and inverting the acquired NMR data in a time domain using petrophysical constraints. The inverted NMR data may then be analyzed. The petrophysical constraints may be identified by determining a number of porobodons to seek, defining a plurality of zones in which only a subset of porobodon sets is present, and stacking all NMR echoes in each zone satisfying discriminators. The number of porobodons to seek may be based on knowledge of core samples, logs, and NMR sensitivity. The discriminator logs may be logs sensitive to porosity partitioning. A computing system having a processor, a memory, and a program stored in memory may be configured to perform the method. The system may be conveyed downhole on a wireline, a while-drilling drill string, a coiled tubing, a slickline, or a wired drill pipe. This summary is provided to introduce a selection of concepts that are further described below in the detailed description. This summary is not intended to identify key or essential features of the claimed subject matter, nor is it intended to be used as an aid in limiting the scope of the claimed subject matter.

FIGURES

Embodiments of a petrophysically regularized NMR inversion in the time domain are described with reference to the following figures. The same numbers are generally used throughout the figures to reference like features and components.

It should be understood that the drawings are not to scale and that the disclosed embodiments are sometimes illustrated diagrammatically and in partial views. In certain instances, details that are not necessary for an understanding of the disclosed method and apparatus or that would render other details difficult to perceive may have been omitted. It should be understood that this disclosure is not limited to the particular embodiments illustrated herein.

DETAILED DESCRIPTION

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", "upstream and downstream", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

In the specification and appended claims, the terms/phrases "connect", "connection", "connected", "in connection with", and "connecting" are used to mean "in direct connection with" or "in connection with via one or more elements", and the term "set" may mean "one element" or "more than one element". Further, the terms "couple", "coupling", "coupled", "coupled together", and "coupled with" are used to mean "directly coupled together" or "coupled together via one or more elements".

Figure 1:
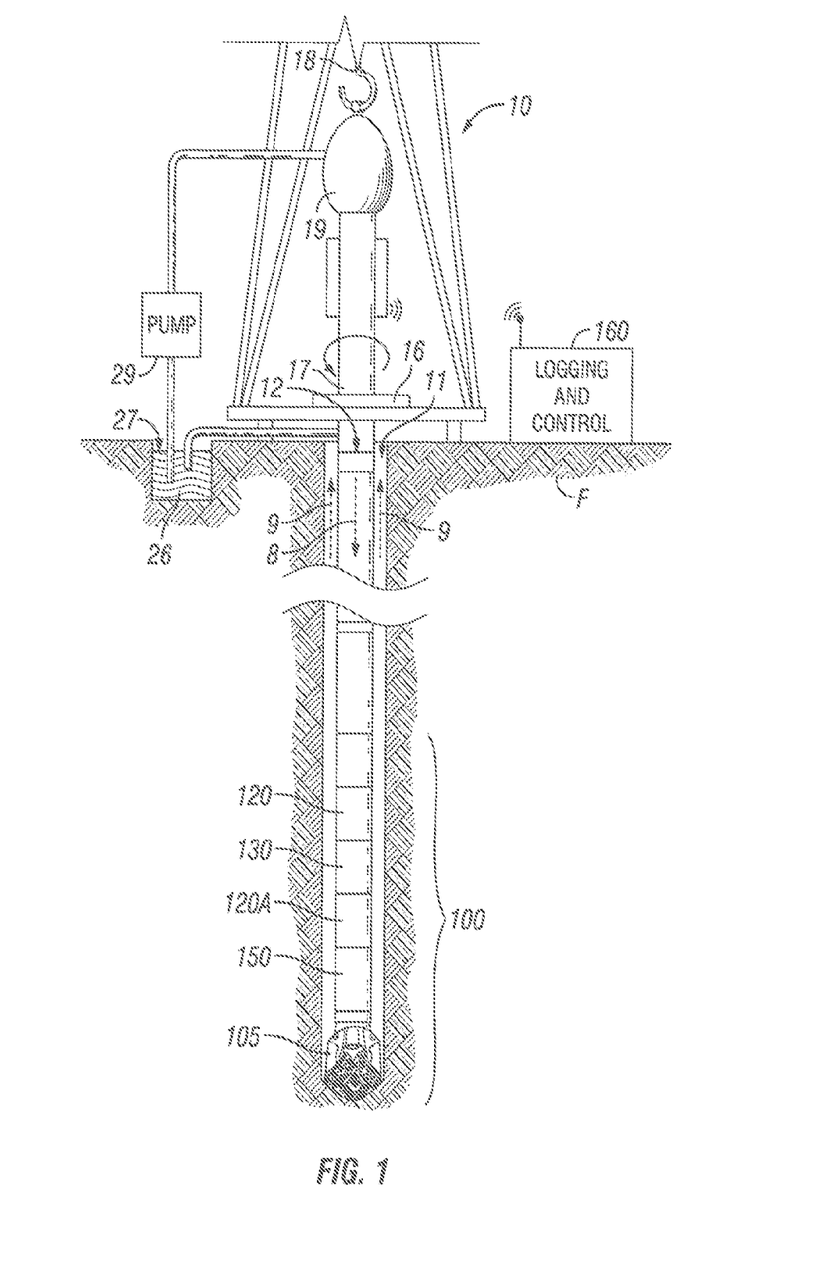
FIG. 1 illustrates a well site system in which various embodiments can be employed.

FIG. 1 illustrates a well site system in which various embodiments can be employed. The well site can be onshore or offshore. In this exemplary system, a borehole 11 is formed in subsurface formations by rotary drilling in a manner that is well known. Some embodiments can also use directional drilling, as will be described hereinafter.

A drill string 12 is suspended within the borehole 11 and has a bottom hole assembly 100 which includes a drill bit 105 at its lower end. The surface system includes platform and derrick assembly 10 positioned over the borehole 11, the assembly 10 including a rotary table 16, kelly 17, hook 18 and rotary swivel 19. The drill string 12 is rotated by the rotary table 16, energized by means not shown, which engages the kelly 17 at the upper end of the drill string. The drill string 12 is suspended from a hook 18, attached to a traveling block (also not shown), through the kelly 17 and a rotary swivel 19 which permits rotation of the drill string relative to the hook. As is well known, a top drive system could alternatively be used.

In the example of this embodiment, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105, and then circulates upwardly through the annulus region between the outside of the drill string and the wall of the borehole, as indicated by the directional arrows 9. In this well known manner, the drilling fluid lubricates the drill bit 105 and carries formation cuttings up to the surface as it is returned to the pit 27 for recirculation.

In various embodiments, the systems and methods disclosed herein can be used with any means of conveyance known to those of ordinary skill in the art. For example, the systems and methods disclosed herein can be used with an NMR tool conveyed by wireline, slickline, drill pipe conveyance, and/or a while-drilling conveyance interface. For the purpose of an example only, FIG. 1 depicts a while-drilling interface. However, systems and methods disclosed herein could apply equally to wireline or any other suitable conveyance means. The bottom hole assembly 100 of the illustrated embodiment includes a logging-while-drilling (LWD) module 120, a measuring-while-drilling (MWD) module 130, a rotary-steerable system and motor 150, and drill bit 105.

The LWD module 120 is housed in a special type of drill collar, as is known in the art, and can contain one or a plurality of known types of logging tools. It will also be understood that more than one LWD and/or MWD module can be employed, e.g. as represented at 120A. (References, throughout, to a module at the position of 120 can alternatively mean a module at the position of 120A as well.) The LWD module includes capabilities for measuring, processing, and storing information, as well as for communicating with the surface equipment. In the present embodiment, the LWD module includes a resistivity measuring device.

The MWD module 130 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick/slip measuring device, a direction measuring device, and an inclination measuring device.

Figure 2:
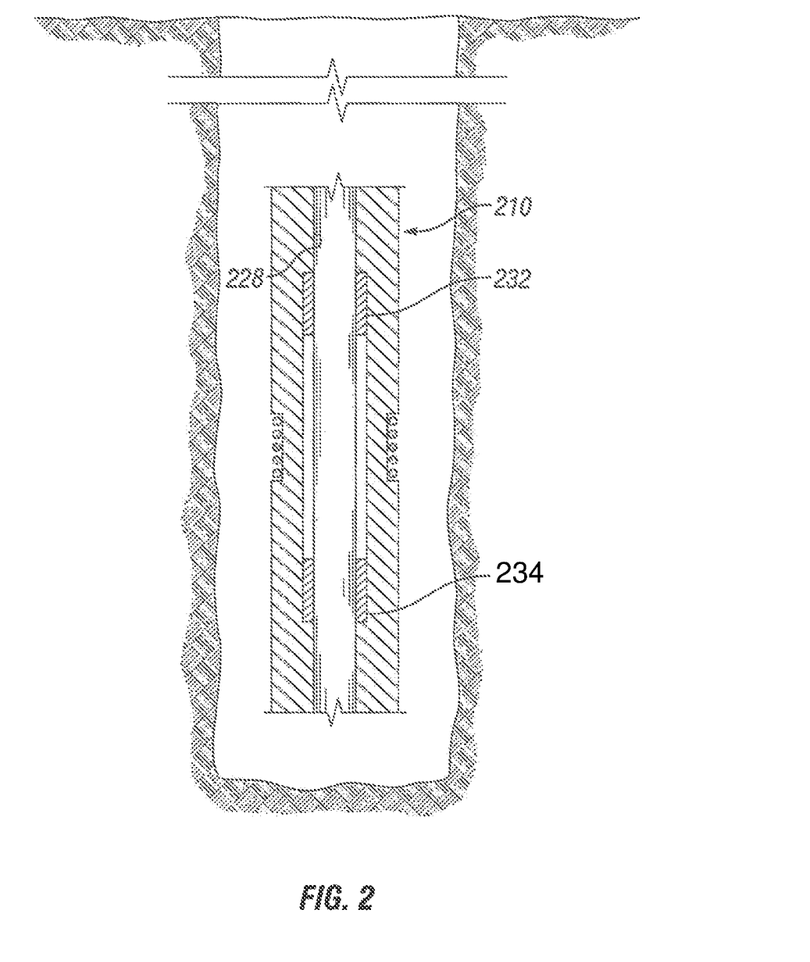
FIG. 2 shows an embodiment of a while-drilling device for formation evaluation using NMR.

FIG. 2 shows an embodiment of a type of device for formation evaluation while drilling using NMR, it being understood that other types of NMR/LWD tools can also be utilized as the LWD tool 120 or part of an LWD tool suite 120A. Referring to FIG. 2, in an exemplary embodiment of the invention, hereinafter referred to as a low gradient design, magnet array comprises an upper magnet 232 axially separated from a lower magnet 234. The area between magnets 232, 234 is suitable for housing elements such as electronic components, an RF antenna, and other similar items. Both magnets 232, 234 surround sleeve 228.

The magnets 232, 234 can be polarized in a direction parallel to the longitudinal axis of the tool 210 with like magnetic poles facing each other. For each magnet 232, 234, the magnetic lines of induction travel outward from an end of the magnet 232, 234 into the formation to create a static field parallel to the axis of the tool 210 and travel inward to the other end of the magnet 232, 234. In the region between upper magnet 232 and lower magnet 234, the magnetic lines of induction travel from the center outward into the formation, creating a static field in the direction perpendicular to the axis of the tool 210. The magnetic lines of induction then travel inward symmetrically above the upper magnet 232 and below the lower magnet 234 and converge in the longitudinal direction inside sleeve 228.

Recent electromagnetic logging tools use one or more tilted or transverse antennas, with or without axial antennas. Those antennas may be transmitters or receivers. A tilted antenna is one whose dipole moment is neither parallel nor perpendicular to the longitudinal axis of the tool. A transverse antenna is one whose dipole moment is perpendicular to the longitudinal axis of the tool, and an axial antenna is one whose dipole moment is parallel to the longitudinal axis of the tool. Two antennas are said to have equal angles if their dipole moment vectors intersect the tool's longitudinal axis at the same angle. For example, two tilted antennas have the same tilt angle if their dipole moment vectors, having their tails conceptually fixed to a point on the tool's longitudinal axis, lie on the surface of a right circular cone centered on the tool's longitudinal axis and having its vertex at that reference point. Transverse antennas obviously have equal angles of 90 degrees, and that is true regardless of their azimuthal orientations relative to the tool.

A system and method are disclosed herein that use a time domain inversion based on a petrophysically restricted stochastic search of Gaussian components directly in the space of pulse decay curves. The disclosed system and method are based on a porobodon/porositon approach. The term "porobodon" has been used to describe a relationship between an NMR relaxation time spectrum and porositon, which in turn is a distinct and separable distribution in maximum pore throat diameters space. See, for example, "Application of Thomeer Hyperbolas to decode the pore systems, facies and reservoir properties of the Upper Jurassic Arab D Limestone, Ghawar field, Saudi Arabia: A "Rosetta Stone" approach", GeoArabia, 2008, v. 13/4, pp. 113-160 by Clerke et al. As used herein, a "porositon" can be considered a distinct and separable frequency distribution of maximum pore throat diameters, $P_d$, which has a Gaussian distribution in the Log($P_d$) domain (i.e., a mode in the maximum pore throat diameter space). Porosity may be characterized by the M Porositon (macroporosity) and Types 1, 2, and 3 Porositons (microporosity). As used herein, a "porobodon" can be considered a postulated mode in the NMR property (e.g., T2, T1, diffusion) distribution that may be directly related to a porositon. While the description herein depicts representative or illustrative embodiments of the disclosed system and method, it should be noted that those of ordinary skill in the art will recognize that the various disclosed embodiments may be applied in many contexts.

Measurements made by NMR tools, such as the illustrated NMR LWD tool 120, are generally input into an inversion process. Various aspects of inverting and otherwise processing NMR-related measurements are discussed herein. Those aspects include: (1) a stochastic inversion estimating porobodon features in a distribution that matches observed pulse decay curves involving petrophysical restrictions on those porobodon features; and (2) a method to determine proper petrophysical restrictions based on the above-mentioned inversion results combined with data from other logs and/or core samples.

In at least some embodiments, a stochastic inversion can include a porobodon/porositon approach to determining an NMR T2 relaxation time distribution, which can be represented as a sum of Gaussian components in a discretized logarithmic time space:

$$\log(T_{2j}) = \log(T_{2min}) + \left(\frac{j-1}{NT_2 - 1}\right) \times [\log(T_{2max}) - \log(T_{2min})] \quad (1)$$

$$amp_j = \sum_{k=1,\ldots NG} a_k \exp\left[-\left(\frac{j-m_k}{\sigma_k}\right)^2\right], j = 1, \ldots NT_2$$

In equation (1), $NT_2$ is the number of discrete T2 bins, which are spaced equally logarithmically between the selected minimum $T_{2min}$ and maximum $T_{2max}$; $T_{2j}$ are the amplitudes and T2 relaxation times of the components $j=1, \ldots NT_2$; and NG is the number of porobodons. Variables in the bottom portion of equation (1) represent porobodon parameters. The variables $a_k$ are called porobodon amplitudes, $m_k$ are porobodon positions, and $\sigma_k$ are porobodon widths. Equation (1) is written for T2, but similar equations can also be specified for T1 and the diffusion coefficient as log-normal distributions for T1 and T2, a normal distribution for the diffusion coefficient, or corresponding combined multi-dimensional distributions for any subset of T1, T2, and the diffusion coefficient.

Restored echoes, $\overline{echo_i}$, (i.e., pulse decay curves) can be reconstructed from these amplitudes as follows:

$$\overline{echo_i} = \sum_{j=1,\ldots NT_2} P(T_{2j}, T_{12r}) K_{ij} amp_j, i = NS, \ldots NE \quad (2)$$

In equation (2), $K_{ij}$ is the NMR kernel matrix, $P(T_{2j}, T_{12r})$ is a polarization correction term depending on T2 and the T1/T2 ratio ($T_{12r}$), and i=NS, . . . NE are sequential echo numbers. Proper kernel equations like equation (2) can be written using methods well known in the art for various pulse sequences used in NMR spectrometry such as CPMG, burst, and/or diffusion editing sequences, both for complete NMR echoes and for window sums. Equations such as equation (2) can also be used for porosity distributions obtained from measured resistivity images and known relationships between formation resistivity and porosity, such as the Archie equation. In such a case, the kernel can be an identity matrix and the effective polarization term corresponds to the pore size sensitivity of the data produced from the resistivity images. In other words, the effective polarization term is typically a Heaviside step function shifted in j-space and designed to cut off shorter times not represented in the porosity distributions obtained from resistivity images.

Theoretically restored echoes, $\overline{echo_i}$, can be compared with measured echoes, $echo_i$, which can be from NMR data, porosity distribution curves, or other data for which some form of equation (2) applies. This means that echoes are represented by the summation of the amplitudes, $amp_j$, defined by equation (1) multiplied by the kernel matrix, $K_{ij}$, and by the polarization term, depending on T2, T1, and the diffusion coefficient.

The differences between measured and restored echoes, $echo_i - \overline{echo_i}$, are assumed to be independent random variables with zero expected value. Taking into consideration a priori data such as the variances of $echo_i - \overline{echo_i}$, one may estimate the probability distribution of $a_k$, $m_k$, and $\sigma_k$ matching the probability distribution of $echo_i - \overline{echo_i}$. In the process of this probability distribution inversion, $a_k$, $m_k$, and $\sigma_k$ are considered to be restricted based on the a priori knowledge:

$$0 \leq a_k \leq a_{k\,max}$$

$$m_{k\,min} \leq m_k \leq m_{k\,max} \quad a_{k\,max} \in \{0, \alpha\infty\}, k=1, \ldots NG$$

$$\sigma_{k\,min} \leq \sigma_k \leq \sigma_{k\,max} \quad (3)$$

Restrictions of the type shown above can be considered petrophysical restrictions. The meaning of the first restriction is that some porobodons are included in the inversion with non-negativity constraints on the amplitude and some are excluded. Also, in addition to $a_k$, $m_k$, and $\sigma_k$, there can be other variables of interest such as porobodon volumes, $V_k = \sqrt{\pi} a_k \sigma_k$, or porobodon volumes normalized by total porosity $\phi$, $$\tilde{V}_k = V_k \phi \bigg/ \sum_{k=1,\ldots NG} V_k.$$

There are various ways to estimate the probability distribution of $a_k$, $m_k$, and $\sigma_k$ given the set of restrictions (3) (or some other derived variables like $V_k$ and $\tilde{V}_k$). For example, Bayesian methods can be used. Any method capable of producing quantiles (such as P10, P50, and P90, for example) and modes of $V_k$, $\tilde{V}_k$, $m_k$, and $\sigma_k$, together with quality control criteria of the inversion itself, can satisfy the requirements for determining proper petrophysical restrictions.

A heuristic method based on a differential evolution stochastic optimization process has been tested and implemented. It can be assumed in some embodiments that mismatches between measured and restored echoes are normally distributed with known standard deviation: $echo_i - \overline{echo_i} \in N(0, \sigma_i)$. Then, the combined weighted normalized mismatch $\Delta$ can be defined to be minimized by the differential evolution process:

$$D = \frac{\sum_{\forall i} w_i \left( \frac{echo_i - \overline{echo_i}}{\sigma_i} \right)^2}{\sum_{\forall i} w_i}, \quad w_i \geq 0 \quad (4)$$

Independent estimates of standard deviations $\sigma_i$ can be used. For example, in the case of NMR, they can be estimated from measurement noise derived from the "minus" signal after phase-alternated pair stacking. However, it may not be necessary to explicitly know $\sigma_i$, as knowledge of their values relative to each other can be sufficient. The mathematical expectation of D according to equation (4) is equal to one. If $\sigma_i = \kappa_i \sigma$, $\kappa_i$ is known, and $\sigma_i$ is substituted with $\kappa_i$ in equation (4), then the expectation of $\Delta$ is equal to $\sigma^2$. In addition, it is not necessary for distributions of $echo_i - \overline{echo_i}$ to be normal as long as they are independent, have zero expectation, and their number is big enough so the central limit theorem applies (for practical purposes, the number should be about 50 or more). Various weights can be assigned to echoes or window sums to enhance or diminish the relative influence of particular parts of echo sequences. These weights must be properly reflected in the coefficients $w_i$ of equation (4).

A differential evolution minimization procedure keeps a population of $a_k$, $m_k$, $\sigma_k$ samples which, upon proper convergence, can be used to sample the probability distributions of $V_k$, $\tilde{V}_k$, $m_k$, and $\sigma_k$ and estimate the quantiles and modes necessary for further analysis. Accordingly, it may be desired to design differential evolution stopping criteria so the population would converge sufficiently; that is, "just enough".

Minimization can be designed as a two-step process. In the first step, a high degree of convergence can be used to get an estimate ($s^2$) of the expectation of the normalized mismatch E(D). The stopping criteria at the first stage can be designed based on the hypothesis testing criteria calculated from the spread of D in the population. Low significance level (i.e., high confidence level, which can be defined as one minus the significance level) can be used at that stage. Upon determining $s^2$, another minimization procedure or procedures can be run with relaxed significance level(s) to sample the area of D around $s^2$. Additionally, several minimization procedures (such as between 3-5 procedures) with different significance levels can be used to sample various ranges of deviation of D from $s^2$. In this case, population sizes of the differential evolution processes corresponding to the different significance levels must be chosen based on the value of the corresponding confidence levels so that the combined population from the populations of all steps with different confidence levels reproduce the distribution of D in the general population. This combined population is then used to estimate parameters of interest such as $a_k$, $m_k$, and $\sigma_k$.

Once the population of $a_k$, $m_k$, $\sigma_k$ has converged to what is considered a proper sample of distributions, quantiles and modes ("best fits") of $a_k$, $m_k$, $\sigma_k$ may be estimated from the population. Quality criteria of the inversion include: (1) confidence level, $p_c$, reached by the minimization procedure first step (i.e., estimating expectation of E(D)); (2) qualitative "yes/no" criteria showing whether the proper confidence levels were reached at subsequent minimization procedure(s) (i.e., sampling the distribution); and (3) if independent estimation of misfit $\sigma^2$ is available (e.g., from NMR noise estimation), the difference, $\Delta$, between $s^2$ and $\sigma^2$ normalized by the theoretical standard deviation of D (in the case of equal weights, $w_i$, in equation (4), $\Delta = (s^2/\sigma^2 - 1)/\sqrt{2/NEcho}$, where Necho is the number of all possible indices i in echoes vector $\overline{echo_i}$). Additional quality control criteria can include: positions of $m_k$, $\sigma_k$ best fits relative to the boundaries of restrictions (3), which should be far enough from restriction boundaries; and percentile values of $m_k$, $\sigma_k$ best fits, which should not be close to 0% or 100%.

Criteria for determining if the inversion results have satisfactory quality include: a high enough confidence level (e.g., $p_c$ at least 95%); a "yes" convergence for the second stage minimization; and a sufficiently low $\Delta$ (less than 3) which can be used as porosity partitioning results (porobodon volumes, positions, and widths). These factors can also be used to determine proper petrophysical restrictions (3) as described below.

As mentioned above, some embodiments can provide a method for determining proper petrophysical restrictions based on above-mentioned inversion results combined with data from other logs and core samples. In other embodiments, other suitable inversions can be used beyond the specific inversions described above, as may be recognized by one of ordinary skill in the art having the benefit of the present disclosure. A priori knowledge about the presence of porobodons in particular zones of the logs is used to determine proper petrophysical restrictions in those zones that are then applied to the whole log.

One can determine the number of porobodons to seek based on knowledge of the core samples, logs, and NMR sensitivity. In a specific example, there may be four porositons observed in the core Macro and Micro 1-3, though it may not be possible to discriminate porobodons corresponding to Micro 2 and 3 in the NMR data since their T2 relaxation times are too short. Accordingly, three porobodons (Macro, Micro 1 and Micro 2/3) are sought. Additional porobodons may be considered to account for fluid effects (e.g., a fourth porobodon for oil wet pores).

After determining the number of porobodons and their broad range of properties based on a priori petrophysical knowledge, zones may be defined in which only a subset of the total porobodon sets is substantially present. Zones can be either one porobodon or more, provided they are clearly resolved in T2 space so that T2 inversions give a T2 distribution with a clear, visible separation of the porobodons. In some embodiments, identification of such zones can be made based on discriminator logs whose values are in one or more intervals specified by an analyst. Alternatively, the intervals may be determined by an automated process based on one or more user-defined criteria. The discriminator logs comprise any that are sensitive to the porosity partitioning. Such discriminator logs can include: (1) commercial T2 distribution bins, as well as the bound fluid volume and the log mean T2 obtained from it; (2) porosity (total NMR, individual NMR bins, neutron, total from ELAN, etc.); (3) mineral volume fractions (e.g., dolomite); (4) NMR first echo amplitude; and (5) depth. In addition to the discrimination on T2 described above, discrimination can also be based on T1 and the diffusion coefficient or combinations of those (including T2) using inversion results.

In at least some embodiments, all echoes in a zone satisfying specified discriminators can be stacked, and then both the commercial and the stochastic inversions described above may be performed for the stacked echoes. In some embodiments, commercial inversion of stacked echoes may be substituted with stacking commercial inversions of individual echoes if the latter are close enough to each other. Restrictions (3) for the distribution of $a_k$ are picked based on the knowledge of which porobodons are present. Restrictions for $m_k$ and $\sigma_k$ are picked as widely as is physically meaningful and/or as widely as a commercial distribution of NMR properties (T2, T1, diffusion coefficient) allows, if there are several distinct porobodons involved. The P10, P50, and P90 quantile best fits (modes) for porobodon volumes, position, and widths may be presented together with measured stacked echoes, echoes restored via stochastic inversion best fit, and echoes restored from a (commercial) distribution of NMR properties.

For visual quality control, a "worm" representing a window averaging result of measured stacked echoes over time may be presented as well. Visual comparison of the "worm" with restored echoes is used instead of the normalized misfit mismatch, $\Delta$, or the quality control of the inversion convergence and quality of the restrictions.

Inversion can be performed interactively with restrictions on the position and width of the selected porobodon being selected as widely as possible until both the visual (i.e., comparison of restored echoes with "worm" and stochastic inversion NMR properties (e.g., T2, T1, diffusion coefficient) distribution with the commercial one) and numerical quality control criteria described above are satisfied.

Once satisfactory inversion results are obtained, the P10 and P90 quantiles of the porobodon positions and widths, for example, may be used as restriction boundaries for these porobodons in all further analyses.

Figure 3:
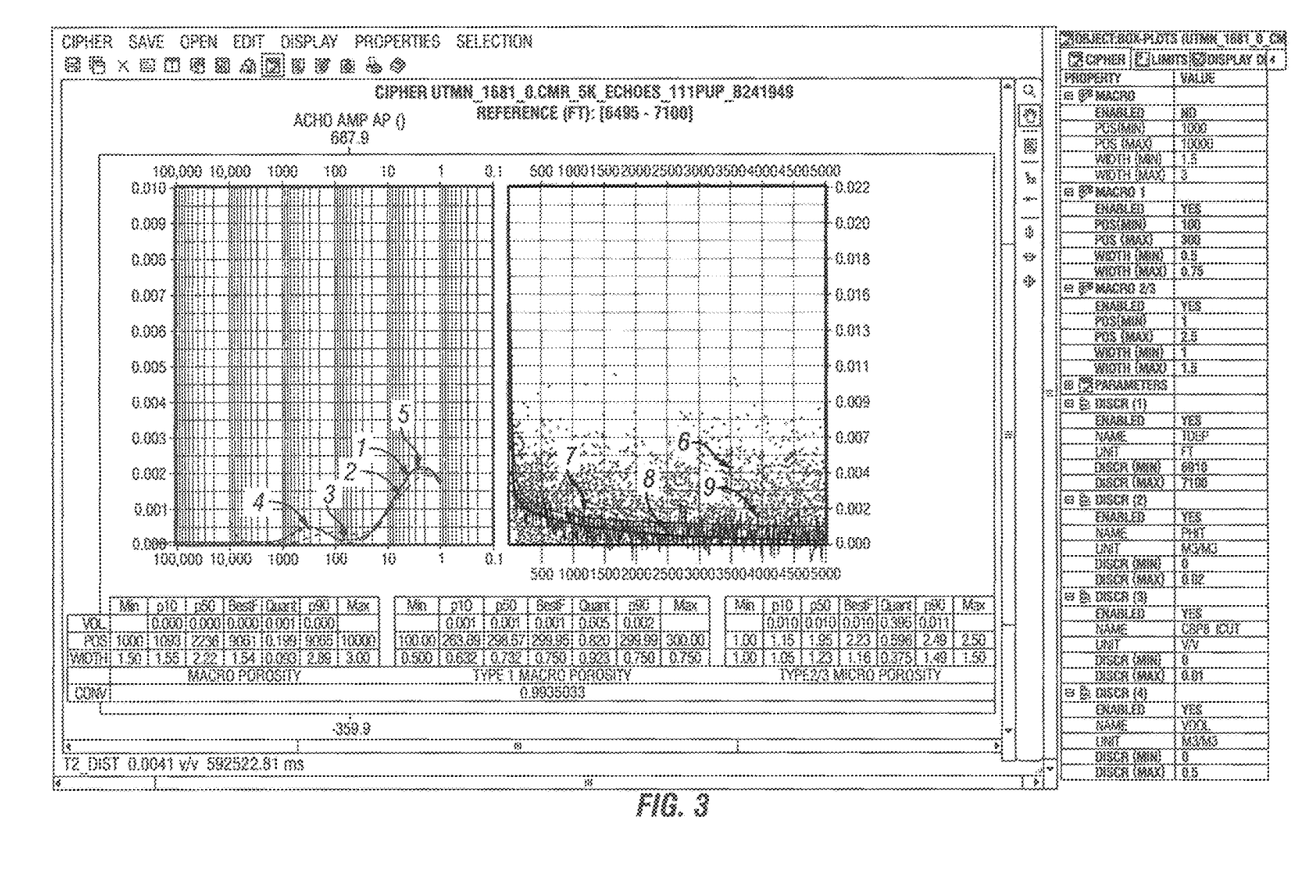
FIG. 3 illustrates an example of inversion results, in accordance with the present disclosure.

FIG. 3 illustrates an example of inversion results consistent with the foregoing description. The plots in FIG. 3 are based on picking the Micro 2/3 (e.g., a combination of Micro2 and Micro3) porobodon. The discriminator used was a specific depth interval and a porosity less than two porosity units (p.u.). The left plot (shown with T2 increasing to the left) illustrates a stochastic inversion (curve 1), a commercial inversion (dashed curve 2), and three individual porobodons (curves 3, 4, and 5). The right plot illustrates echoes, including stacked measured echoes (dots 6), echoes restored from a commercial inversion (dashed curve 7 and curve 8), and worm echoes (curve 9). Inversion results are shown near the bottom of the plots. The strip below the inversion results indicates a good (99%) confidence level. Restrictions are shown to the right of the plots.

In at least some embodiments, one may further determine a zone in which only one new porobodon, in addition to the porobodons for which restrictions are already defined, is substantially present. (There can be more than one porobodon if these new porobodons are clearly distinct on commercial T2 distributions.) Stacking and inversion as described above may be performed as well. Restrictions for the new porobodons are selected as widely as possible within the quality control criteria. P10 and P90 quantiles may again be used in all further analyses as restriction boundaries of these new porobodon positions and widths.

Figure 4:
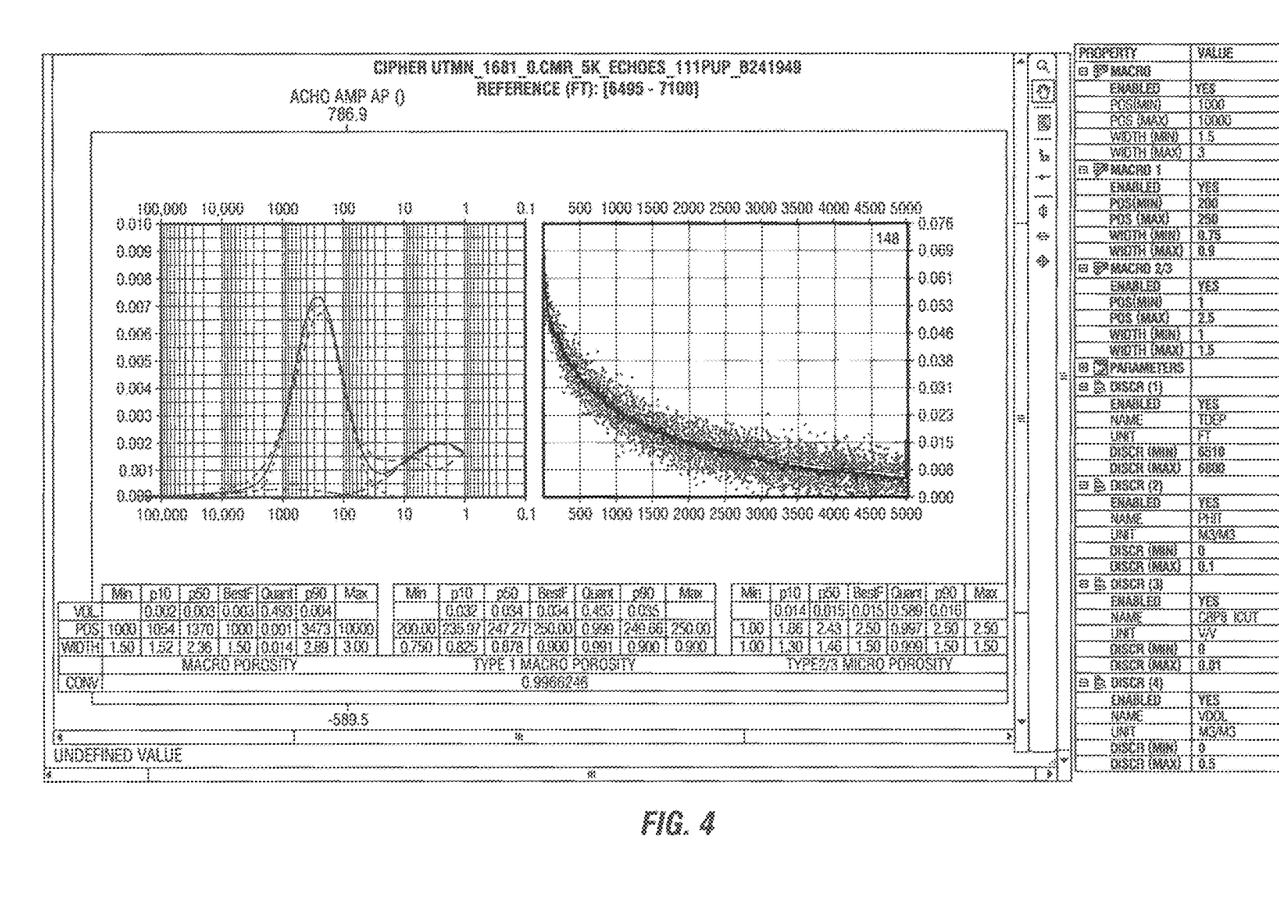
FIG. 4 illustrates another example of inversion results, in accordance with the present disclosure.

FIG. 4 illustrates another example of inversion results consistent with the foregoing description. The plots in FIG. 4 are based on picking the Micro 1 porobodon. The discriminators in this case include a depth interval, a volume of dolomite less than 0.5 cm$^3$, a porosity less than 0.1 p.u., and an NMR porosity (in a bin corresponding to T2s greater than two seconds) that is less than 0.01 p.u. Those cutoffs are selected by an analyst or automated process based on the log responses and knowledge of the formation.

Figure 5:
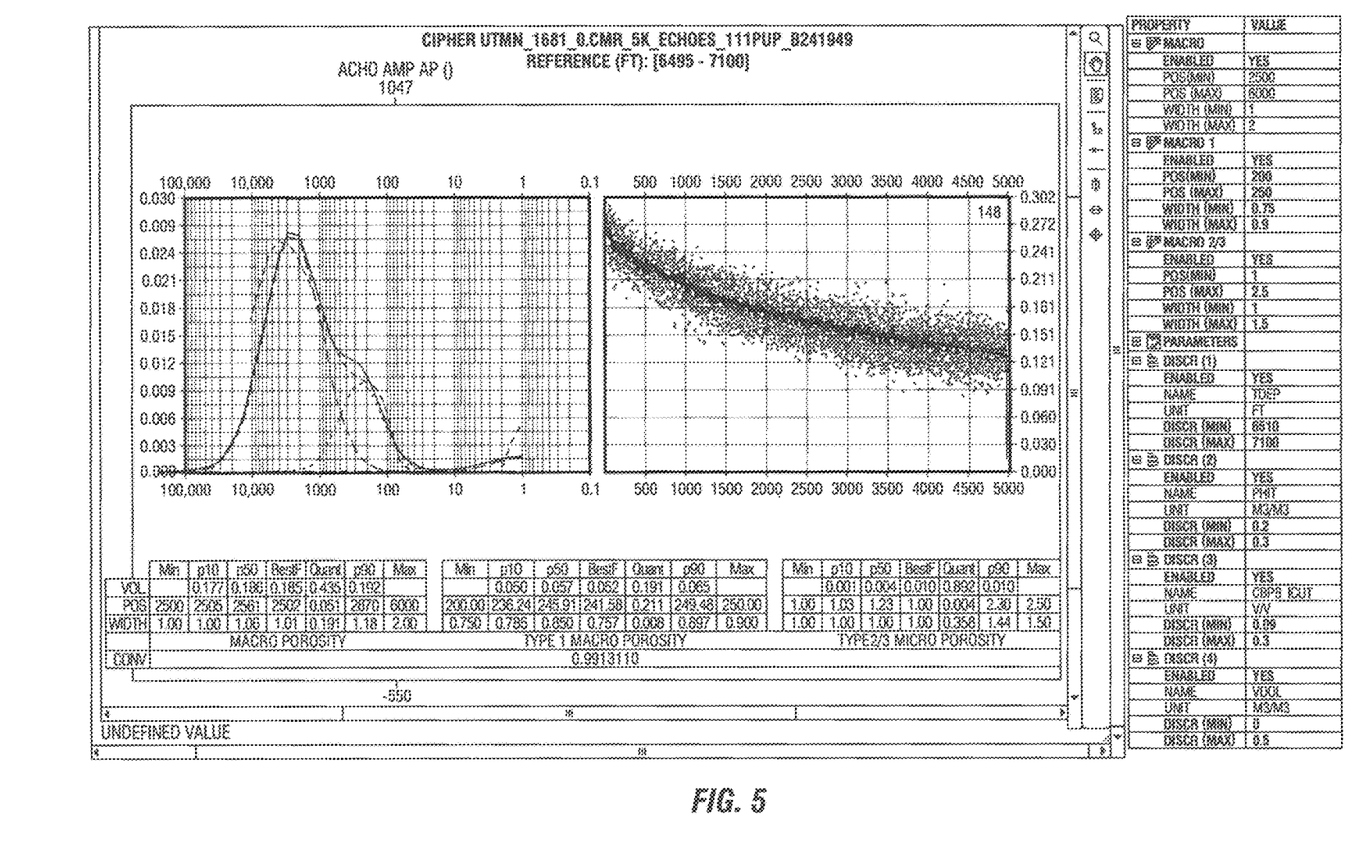
FIG. 5 illustrates another example of inversion results, in accordance with the present disclosure.

FIG. 5 illustrates another example of inversion results consistent with the foregoing description. The plots in FIG. 5 are based on picking the Macro porobodon. The discriminators include a depth interval, a volume of dolomite less than 0.5 cm$^3$, a porosity between 0.2 and 0.3 p.u., and an NMR porosity (in a bin corresponding to T2s greater than two seconds) between 0.1 and 0.3 p.u. Again, those cutoffs are selected by an analyst or automated process based on log responses and knowledge of the formation. Restriction determination as described above is iteratively performed until all the restrictions for porobodon positions and widths are defined.

The embodiments presented herein are illustrative, and, in alternative embodiments, certain steps or structural elements may be performed or assembled in a different order, in parallel with one another, omitted entirely, and/or combined with or without certain additional steps or structures. Accordingly, such alternative embodiments are included in the present disclosure.

Figure 6:
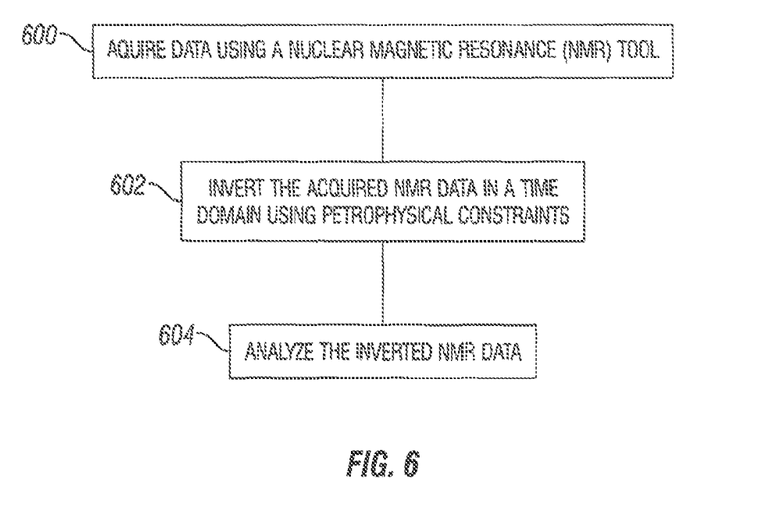
FIG. 6 is a flowchart of an example embodiment that comprises a computer program that embodies the functions described herein, in accordance with the present disclosure.

The method and system disclosed herein may comprise a computer program that embodies the functions described herein and shown in the flowchart of FIG. 6. In this embodiment, data is acquired using a nuclear magnetic resonance tool (step 600). The acquired NMR data are inverted in a time domain using petrophysical constraints (step 602). The inverted NMR data may then be analyzed (step 604). It should be apparent that there could be many different ways of implementing the method disclosed herein in a computer or other programmable device, and the method disclosed herein should not be construed as limited to any one set of program instructions. Further, a skilled programmer would be able to write such a program to implement an embodiment of the method disclosed herein based on the flow charts and associated description. Therefore, disclosure of a particular set of program code instructions is not considered necessary for an adequate understanding of how to make and use the method and system disclosed herein.

The method and system disclosed herein can be used with computer hardware and software that performs the functions described above. Specifically, any or all of those functions can be performed using an automated or computerized process. As will be appreciated by those skilled in the art, the method and system described herein can be embodied in a programmable computer, computer executable software, or digital circuitry. The software can be stored on computer readable media, such as non-transitory computer readable media. For example, computer readable media can include a floppy disk, random access memory (RAM), read only memory (ROM), a hard disk, removable media, flash memory, a memory stick, optical media, magneto-optical media, a CD-ROM, etc. Digital circuitry can include integrated circuits, gate arrays, building block logic, field programmable gate arrays (FPGA), etc.

Figure 7:
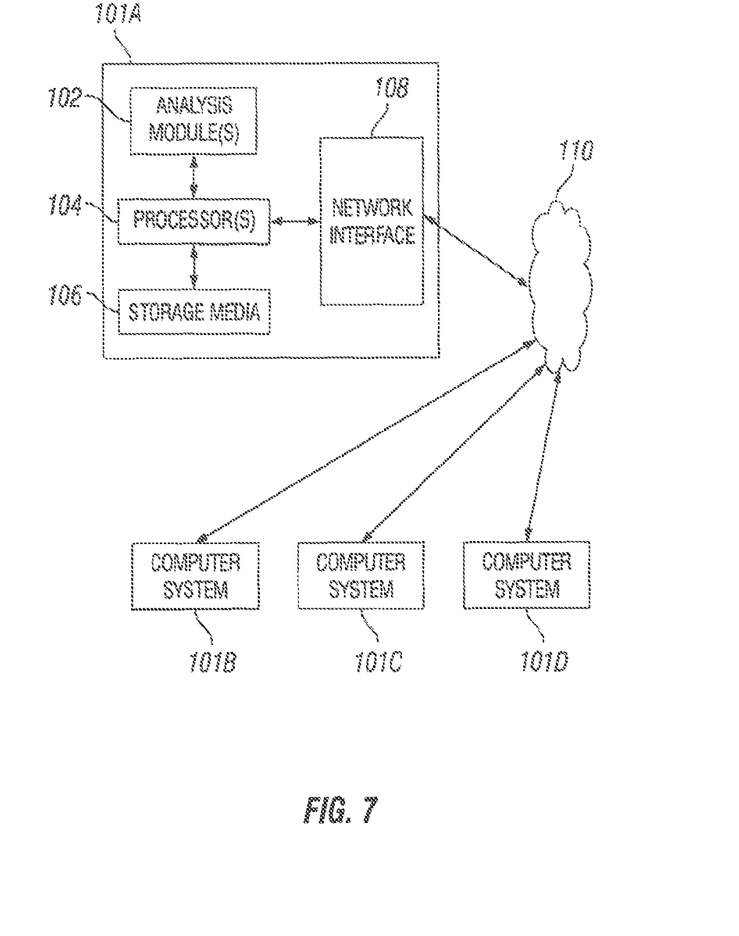
FIG. 7 illustrates a computing system, in accordance with the present disclosure.

The computing system shown in FIG. 7 can be an individual computer system 101A or an arrangement of distributed computer systems. The computer system 101A includes one or more analysis modules 102 that are configured to perform various tasks according to some embodiments, such as one or more methods disclosed herein (e.g., any of the steps, methods, techniques, and/or processes, and/or combinations and/or variations and/or equivalents thereof). To perform these various tasks, analysis module 102 executes independently, or in coordination with, one or more processors 104, which is (or are) connected to one or more storage media 106. The processor(s) 104 is (or are) also connected to a network interface 108 to allow the computer system 101A to communicate over a data network 110 with one or more additional computer systems and/or computing systems, such as 101B, 101C, and/or 101D (note that computer systems 101B, 101C and/or 101D may or may not share the same architecture as computer system 101A, and may be located in different physical locations, e.g. computer systems 101A and 101B may be on a ship underway on the ocean, while in communication with one or more computer systems such as 101C and/or 101D that are located in one or more data centers on shore, on other ships, and/or located in varying countries on different continents).

A processor can include a microprocessor, microcontroller, processor module or subsystem, programmable integrated circuit, programmable gate array, or another control or computing device.

The storage media 106 can be implemented as one or more computer-readable or machine-readable storage media. Note that while in the example embodiment of FIG. 7 storage media 106 is depicted as within computer system 101A, in some embodiments, storage media 106 may be distributed within and/or across multiple internal and/or external enclosures of computing system 101A and/or additional computing systems. Storage media 106 may include one or more different forms of memory including semiconductor memory devices such as dynamic or static random access memories (DRAMs or SRAMs), erasable and programmable read-only memories (EPROMs), electrically erasable and programmable read-only memories (EE-PROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system is only one example of a computing system, and that computing system may have more or fewer components than shown, may combine additional components not depicted in the example embodiment of FIG. 7, and/or the computing system may have a different configuration or arrangement of the components depicted in FIG. 7. For example, though not shown explicitly, the computing system would generally include input and output devices such as a keyboard, a mouse, a display monitor, and a printer and/or plotter. The various components shown in FIG. 7 may be implemented in hardware, software, or a combination of both hardware and software, including one or more signal processing and/or application specific integrated circuits.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method, comprising:
    using a nuclear magnetic resonance (NMR) tool to acquire NMR data from a wellbore traversing a subterranean formation, wherein the NMR data includes at least one of NMR distributions of T1, T2, or diffusion coefficient, and wherein petrophysical constraints comprise intervals for distribution parameters related to T1, T2, and diffusion;

inverting the acquired NMR data in a time domain using petrophysical constraints comprising $$0 \le a_k \le a_{kmax}$$
$$m_{kmin} \le m_k \le m_{kmax} \quad a_{kmax} \in \{0, +\infty\}, k = 1, \ldots NG,$$
$$\sigma_{kmin} \le \sigma_k \le \sigma_{kmax}$$

wherein $a_k$ are porobodon amplitudes, $m_k$ are porobodon positions, $\sigma_k$ are porobodon widths, and NG is a number of porobodons;

analyzing the inverted NMR data to determine a characteristic of a fluid in the subterranean formation; and using the determined characteristic of the fluid in the subterranean formation in an oilfield operation or evaluation.

2. The method of claim 1, wherein inverting the acquired NMR data is applied to a one-dimensional distribution of a relaxation time T1, a relaxation time T2, or a diffusion coefficient; a multi-dimensional distribution of the relaxation time T1, the relaxation time T2, and the diffusion coefficient; or a subset of those distributions.

3. The method of claim 2, wherein the subset of those distributions includes a distribution based on a priori petrophysical knowledge.

4. The method of claim 2, wherein the subset of those distributions includes linear superpositions of log-normal distributions for the relaxation time T1 and the relaxation time T2 and a normal distribution for the diffusion coefficient.

5. The method of claim 1, wherein inverting the acquired NMR data is performed according to the equations:

$$\log(T_{2j}) = \log(T_{2min}) + \left(\frac{j-1}{NT_2 - 1}\right) \times [\log(T_{2max}) - \log(T_{2min})]$$

$$amp_j = \sum_{k=1,\ldots NG} a_k \exp\left[-\left(\frac{j - m_k}{\sigma_k}\right)^2\right], j = 1, \ldots NT_2$$

wherein $NT_2$ is a number of discrete T2 bins, which are spaced equally logarithmically between a selected minimum $T_{2min}$ and maximum $T_{2max}$; $T_{2j}$ are amplitudes and $T_2$ relaxation times of components $j=1, \ldots NT_2$, amp is amplitude, $a_k$ are porobodon amplitudes, $m_k$ are porobodon positions, and $\sigma_k$ are porobodon widths.

6. The method of claim 1, further comprising reconstructing pulse decay curves according to an equation in which echoes are represented by a summation of amplitudes $amp_j$ of a one-dimensional distribution of T1, T2, or the diffusion coefficient; a multi-dimensional distribution of T1, T2 and the diffusion coefficient; or any subset of those quantities; multiplied by a kernel matrix $K_{ij}$ and by a polarization term that depends on T2, T1, and the diffusion coefficient.

7. The method of claim 1, further comprising reconstructing pulse decay curves according to the equation:

$$\overline{echo_i} = \sum_{j=1,\ldots NT_2} P(T_{2j}, T_{12r}) K_{ij} amp_j, i = NS, \ldots NE.$$

wherein $\overline{echo_i}$ are restored echoes, $K_{ij}$ is a NMR kernel matrix, $P(T_{2j}, T_{12r})$ is a polarization correction term depending on T2 and T1/T2 ratio ($T_{12r}$), and $i=NS, \ldots NE$ are sequential echo numbers.

8. The method of claim 1, further comprising estimating a porobodon features distribution that matches observed pulse decay curves involving petrophysical restrictions on the porobodon features.

9. The method of claim 1, wherein the petrophysical constraints are identified by:

determining a number of porobodons to seek;

defining a plurality of zones in which only a subset of porobodon sets is present; and stacking all NMR echoes in each zone satisfying discriminators.

10. A method, comprising:

using an NMR tool to acquire NMR echoes from a wellbore traversing a subterranean formation;

determining a number of porobodons to seek;

defining a plurality of zones or discriminator cutoffs in which only a subset of porobodon sets is present based on discriminator logs whose values are in specified intervals, wherein the discriminator logs are selected from a group consisting of: commercial T2 distribution bin logs, porosity logs, mineral volume fraction logs, NMR first echo amplitude logs, and depth logs;

stacking all NMR echoes in each zone satisfying discriminators;

identifying petrophysical constraints based on a priori knowledge;

inverting the acquired NMR echoes using the identified petrophysical constraints;

using P10/P90 results of the inversion as petrophysical restrictions for further analyses, wherein P10 and P90 represent quantile best fits for porobodon volumes, determining a characteristic of a fluid in the subterranean formation based on the analyses; and using the determined characteristic of the fluid in the subterranean formation in an oilfield operation or evaluation.

11. The method of claim 10, wherein the number of porobodons to seek is based on knowledge of core samples, logs, and NMR sensitivity.

12. The method of claim 10, wherein the discriminator logs comprise logs sensitive to a porosity partitioning.

13. The method of claim 10, wherein the acquired NMR echoes are inverted in a time domain.

* * * * *